(12) United States Patent
Katcha et al.

(10) Patent No.: US 7,054,411 B2
(45) Date of Patent: May 30, 2006

(54) MULTICHANNEL CONTACTLESS POWER TRANSFER SYSTEM FOR A COMPUTED TOMOGRAPHY SYSTEM

(75) Inventors: Jason Stuart Katcha, Whitefish Bay, WI (US); Jonathan Richard Schmidt, Wales, WI (US); Marcela Gonzalez, Wauwatosa, WI (US); Phil E. Pearson, Jr., Hartland, WI (US)

(73) Assignee: General Electric Company, Schenectady, NY (US)

( * ) Notice: Subject to any disclaimer, the term of this patent is extended or adjusted under 35 U.S.C. 154(b) by 111 days.

(21) Appl. No.: 10/708,934

(22) Filed: Apr. 1, 2004

(65) Prior Publication Data

US 2005/0226380 A1    Oct. 13, 2005

(51) Int. Cl.
*H05G 1/10* (2006.01)

(52) U.S. Cl. .................... 378/101; 378/15; 336/105

(58) Field of Classification Search ............. 378/15, 378/101; 336/105
See application file for complete search history.

(56) References Cited

U.S. PATENT DOCUMENTS

| 3,893,015 A | * | 7/1975 | Weil | 363/27 |
|---|---|---|---|---|
| 4,672,528 A | | 6/1987 | Park et al. | 363/98 |
| 4,912,735 A | * | 3/1990 | Beer | 378/15 |
| 5,023,768 A | * | 6/1991 | Collier | 363/68 |
| 5,449,979 A | * | 9/1995 | Ueoka et al. | 315/225 |
| 5,451,878 A | | 9/1995 | Wirth et al. | 324/322 |
| 5,608,771 A | * | 3/1997 | Steigerwald et al. | 378/15 |
| 5,646,835 A | | 7/1997 | Katcha | 363/98 |
| 6,301,324 B1 | | 10/2001 | Pearson, Jr. et al. | 378/15 |
| 6,674,836 B1 | * | 1/2004 | Harada et al. | 378/107 |
| 2002/0067631 A1 | * | 6/2002 | Lunding et al. | 363/131 |
| 2005/0018815 A1 | * | 1/2005 | Loef et al. | 378/101 |

* cited by examiner

*Primary Examiner*—Edward J. Glick
*Assistant Examiner*—Krystyna Suchecki
(74) *Attorney, Agent, or Firm*—Cantor Colburn LLP

(57) ABSTRACT

A multichannel, contactless power transfer system includes a primary power inverter disposed on a stationary side of the system, and an auxiliary power inverter disposed on the stationary side of the system. A rotary transformer has a primary side thereof disposed on the stationary side of the system and a secondary side disposed on a rotating side of the system. The rotary transformer is configured to couple primary power from an output of the primary power inverter to a primary power voltage output on the rotating side of the system, and is further configured to couple auxiliary power from an output of the auxiliary power inverter to at least one auxiliary voltage output on the rotating side of the system.

16 Claims, 6 Drawing Sheets ns cases, it is advantageous to reduce the volume

MULTICHANNEL CONTACTLESS POWER TRANSFER SYSTEM FOR A COMPUTED TOMOGRAPHY SYSTEM

BACKGROUND OF THE INVENTION

The present disclosure relates generally to power transfer mechanisms and, more particularly, to a multichannel, contactless power transfer system for a computed tomography (CT) system.

Computed tomography (CT) systems are used to obtain non-invasive sectional images of test objects, particularly internal images of human tissue for medical analysis and treatment. Current CT systems position the test object, such as a patient, on a table within a central aperture of a rotating frame, or gantry, which is supported by a stationary frame. The gantry includes an x-ray source and a detector array positioned on opposite sides of the aperture, within an x-y plane of a Cartesian coordinate system (generally referred to as the "imaging plane"), such that both rotate with the gantry around the test object being imaged. At each of several angular positions along the rotational path of the gantry (also referred to as "projections"), the x-ray source emits a fan-shaped collimated beam that passes through the imaging slice of the test object, is attenuated by the test object, and is received by the detector array.

Each detector element in the detector array produces a separate electrical signal indicative of the attenuated x-ray beam intensity, the beam projected from the x-ray source to the particular detector element, incident at its sensor surface. The electrical signals from all the detector elements are collated by circuitry within the rotating frame to produce a projection data set at each gantry angle or projection. Each projection data set is referred to as a "view", and a "scan" is a set of such views from the different gantry angles during one revolution of the x-ray source and detector array. The scan is then processed by a computer in the stationary frame to reconstruct the projection data sets into a CT image of the slice or cross-section of the test object.

In a conventional CT system, power is transferred across a brush and slip ring mechanism to an inverter, which physically rotates with the gantry along with a high-voltage tank circuit (e.g., including transformer, rectifier, and filter capacitance components) of the CT system. Unfortunately, placing the inverter on the rotational gantry increases the weight, volume and complexity of the system. Furthermore, brush and slip ring mechanisms (which are typically used to carry appreciable current) are subject to reduced reliability, maintenance problems, and electrical noise generation, which interferes with sensitive modern medical diagnostic procedures, especially in harsh environments.

Accordingly, as higher rotational speed CT systems are developed, it becomes advantageous to reduce the volume and weight of the rotating components.

BRIEF DESCRIPTION OF THE INVENTION

The above discussed and other drawbacks and deficiencies of the prior art are overcome or alleviated by a multichannel, contactless power transfer system. In an exemplary embodiment, the power transfer system includes a primary power inverter disposed on a stationary side of the system, and an auxiliary power inverter disposed on the stationary side of the system. A rotary transformer has a primary side thereof disposed on the stationary side of the system and a secondary side disposed on a rotating side of the system. The rotary transformer is configured to couple primary power from an output of the primary power inverter to a primary power voltage output on the rotating side of the system, and is further configured to couple auxiliary power from an output of the auxiliary power inverter to at least one auxiliary voltage output on the rotating side of the system.

In another embodiment, a multichannel, contactless power transfer system for a computed tomography (CT) system includes an x-ray power inverter disposed on a stationary side of the CT system, and an auxiliary power inverter disposed on the stationary side of the CT system. A rotary transformer has a primary side thereof disposed on the stationary side of the CT system and a secondary side disposed on a rotating side of the CT system. The rotary transformer is configured to couple x-ray generation power from an output of the x-ray power inverter to a high-voltage tank circuit on the rotating side of the CT system, wherein the high-voltage tank circuit is further coupled to an x-ray generation tube. The rotary transformer is further configured to couple auxiliary power from an output of the auxiliary power inverter to at least one auxiliary voltage output on the rotating side of the CT system.

In still another embodiment, a multichannel rotary transformer includes a stationary side and a rotating side, each having a pair of concentric, E-shaped cores. One of the pair of concentric, E-shaped cores is configured to couple primary power from the stationary side to the rotating side, and the other of the pair of concentric, E-shaped cores is further configured to couple auxiliary power from the stationary side to the rotating side.

BRIEF DESCRIPTION OF THE DRAWINGS

Referring to the exemplary drawings wherein like elements are numbered alike in the several Figures.

DETAILED DESCRIPTION OF THE INVENTION

Disclosed herein is a multichannel, contactless power transfer system for a CT system that provides both X-ray generator and auxiliary power to the rotating portion of the CT system through the use of a multiple channel rotary transformer. Thus, the non-contacting manner in which power is transferred (i.e., through electromagnetic induction) is used for all of the CT system power transfer needs. Thereby, the CT system is characterized by a reduced complexity, in that a greater number of components may be removed from the rotating side of the gantry. In addition, the present invention embodiments further address radiated EM noise and other details of the rotary transformer windings for adapting a multichannel, contactless power transfer system to a CT system.

Figure 1:
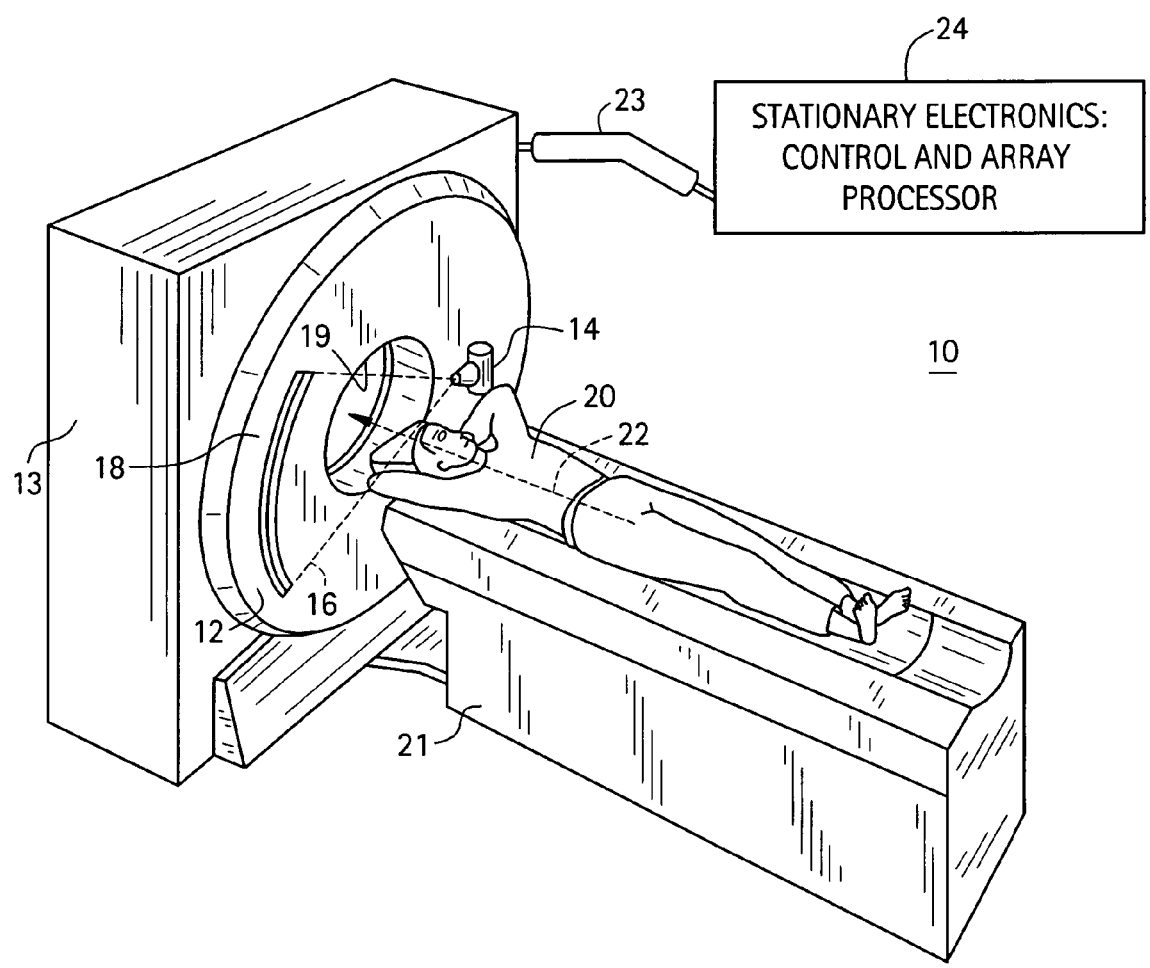
FIG. 1 is an exemplary computerized tomography (CT) system 10 suitable for use in accordance with an embodiment of the invention.

Referring initially to FIG. 1, there is shown an exemplary computerized tomography (CT) system 10 suitable for use in accordance with an embodiment of the invention. The system 10 includes a generally annular rotating frame 12 or gantry, as well as a stationary frame 13 that supports the rotating frame 12. The rotating frame 12 further includes an x-ray source 14 for emitting a highly collimated x-ray beam 16 toward a detector array 18 positioned on the opposite side of an aperture 19. Aperture 19 permits a test object 20 (such as a patient) to be placed on a platform 21 which may be movable, for example, by translation, along a rotational axis 22 of the rotating frame 12. The movement of platform 21 allows different cross-sectional portions of interest of the test object 20 to be positioned within the imaging plane of the rotating frame 12.

Once the test object 20 has been positioned within aperture 19, such as through movement of the test object 20 and/or platform 21, the rotating frame 12 is then rotated about the rotational axis 22, and at each of a plurality of angular positions along the rotational path. Concurrently, the x-ray source 14 emits x-ray beam 16, which passes through the test object 20 and is incident on the receiving surfaces of a plurality of detector elements (not individually shown) of the detector array 18. In response, each of the detector elements of detector array 18 produces an electrical signal at a magnitude proportional to the intensity of the received rays, and thus to the amount of attenuation of the x-ray beam after passing through the test object 20.

The signals from each of the detector elements of detector array 18, which represent the projection data, are transmitted through lines 23 to a control and array processor 24 that processes the received projection data into a radial image of test object 20 at the selected radial or angular position, which is referred to as a view. Then, the aggregate of the views taken over a full revolution of the rotating frame 12, generally referred to as a scan, are further processed, using known image processing algorithms, into a cross-sectional image of the portion of interest of test object 20 that was within the imaging plane.

Although not illustrated specifically in FIG. 1, in a conventionally configured power transfer arrangement, several of the power transfer electronic assemblies (e.g., the inverter, high-voltage tank circuit) are also physically mounted to the rotating frame 12, in addition to the x-ray source 14 and detector array 18. Unfortunately, the desired ability of rotating the rotating frame 12 at increasing speeds is compromised by (among other factors) the mass of the electronic components. As the gantry speed increases, so does the power requirement of the generator in order to maintain a constant signal to noise ratio (SNR). Thus, the mass of the generator components is increased as a consequence. This in turn results in the need to cantilever such components out from the rotating frame 12, thereby adding torque to the mounting brackets and amplifying the forces thereon, which further limits rotational speed.

Figure 2:
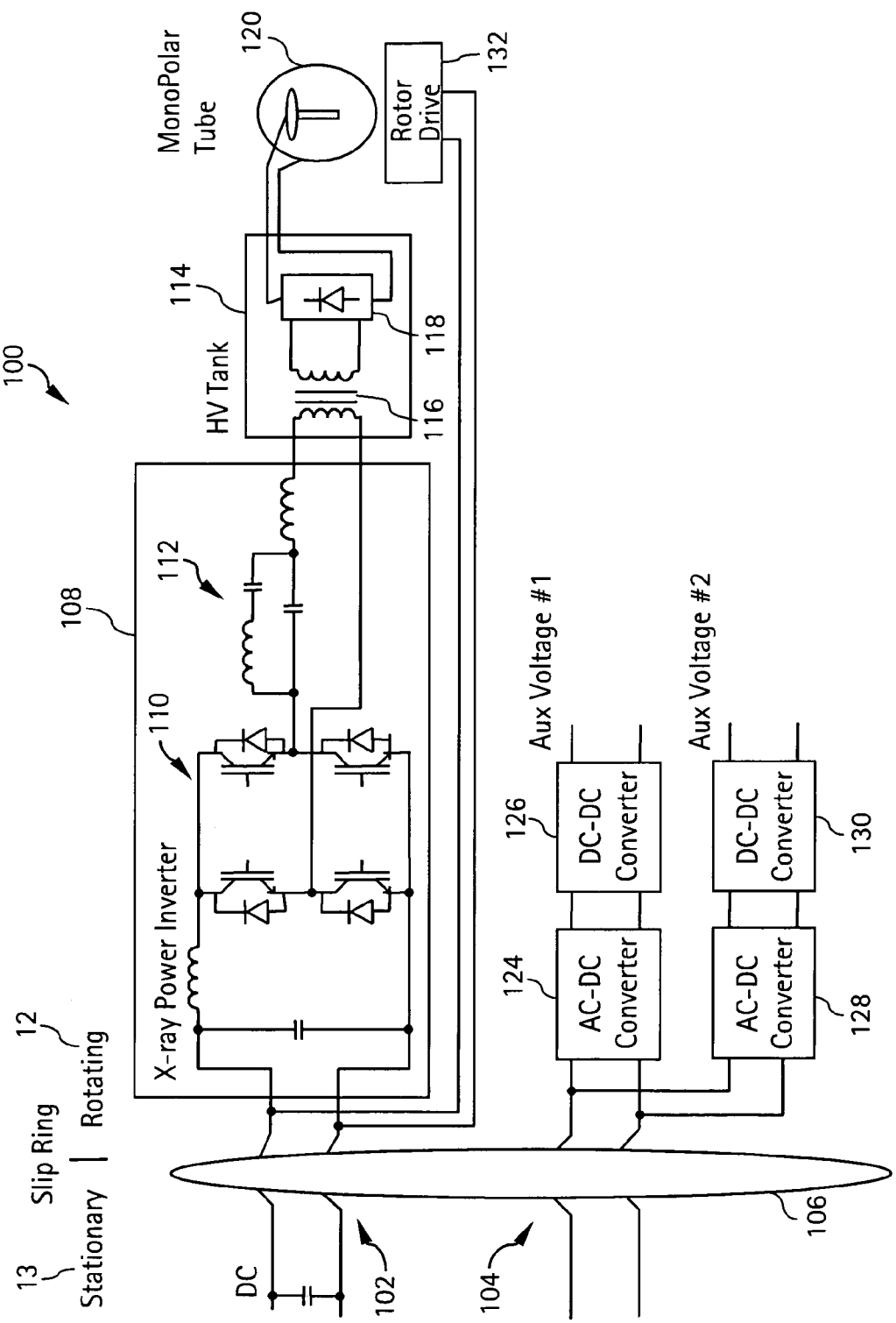
FIG. 2 is a schematic diagram of an existing power transfer system for CT applications.

FIG. 2 is a schematic diagram of an existing power transfer system 100 for CT applications, including a primary power channel 102 for transferring x-ray generator power and at least one secondary power channel 104 for transferring auxiliary power used for many of the electronic devices located on the rotating frame 12. As is shown, power from the primary and secondary power channels is transferred from the stationary frame 13 to the rotating frame 12 in a "contacting" manner, represented by slip ring 106. In particular, the x-ray generator power transferred through primary power channel 102 is controlled by a gantry-mounted x-ray power inverter 108, which is supplied by a DC voltage through slip ring 106. The inverter 108 includes four insulated gate bipolar transistor (IGBT) switches (denoted generally at 110) that are used to generate a high frequency current and voltage. One leg of the AC output side of the inverter 108 includes resonant inductive and capacitive components that form a series-resonant circuit 112 for creating a sinusoidal current waveform that reduces IGBT switching losses, as well as radiated electromagnetic emissions.

The AC output voltage from inverter 108 is fed to a high-voltage (HV) tank circuit 114 that generates a high-voltage DC potential through a step-up transformer 116 and rectifier circuits 118. The HV DC potential (e.g., 140 kV) is then applied to x-ray tube 120 for generation of x-rays.

As shown in the secondary power channel 104, input AC power from the stationary frame 13 also is transferred in a contacting manner (i.e., via slip ring) to the rotating frame 12 for conversion to auxiliary power voltages. In the example depicted, a first auxiliary voltage is produced through a first AC/DC converter 124 configured in series with a first DC/DC converter 126, while a second auxiliary voltage on the rotating frame 12 is produced through a second AC/DC converter 128 configured in series with a second DC/DC converter 130. It will be appreciated that the AC/DC and DC/DC converter parameters may be selected to produce any desired DC auxiliary voltage values, depending on the type of load(s) to be supplied therefrom. Finally, FIG. 2 further depicts a rotor drive 132 used for driving the rotor of the x-ray tube 120, wherein the power thereto is taken directly from the DC power transferred through the slip ring 106.

Figure 3:
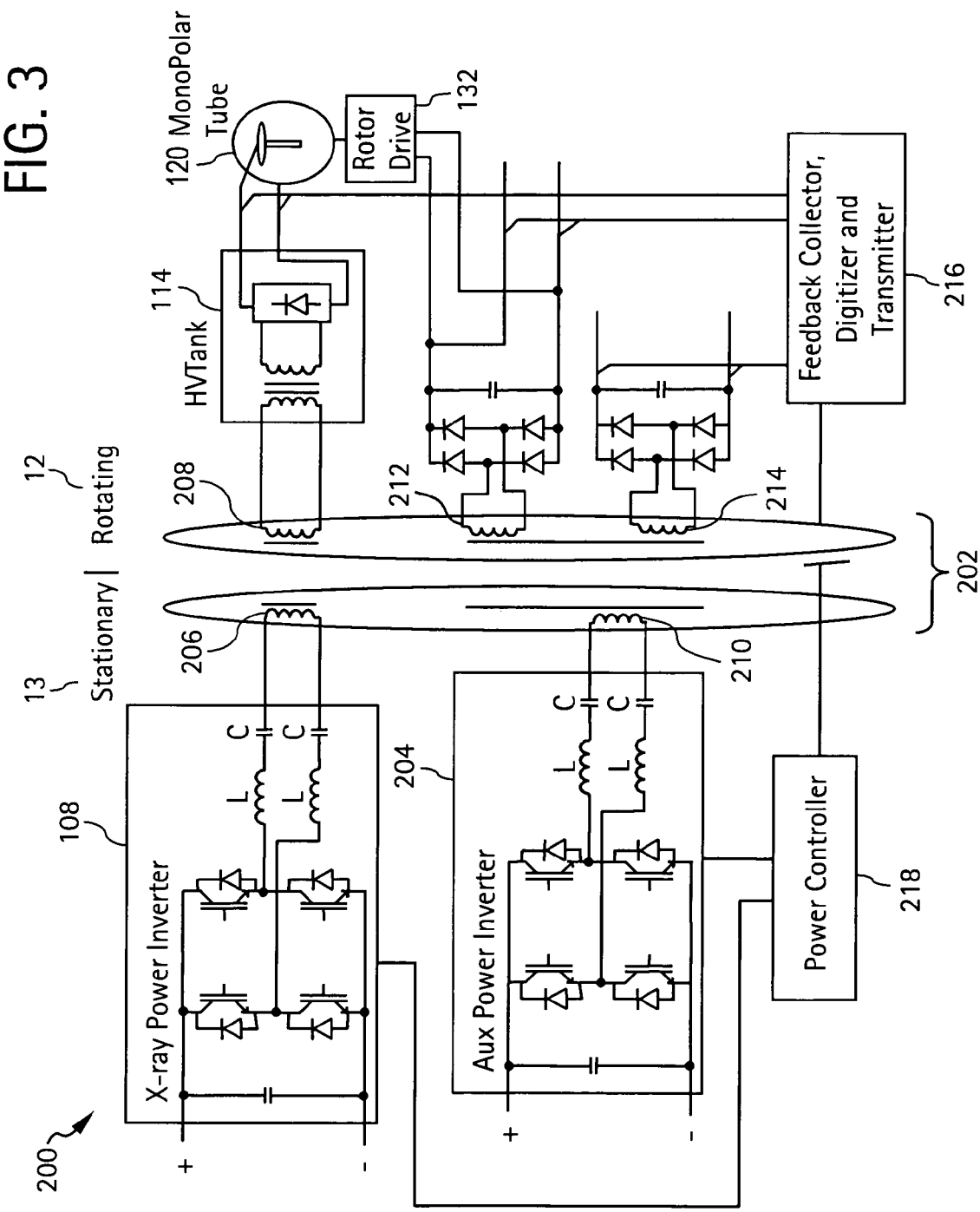
FIG. 3 is a schematic diagram of a multichannel, contactless power transfer system for a CT system, in accordance with an embodiment of the invention.

However, as indicated previously, the placement of power conversion electronics on the placing on the rotational gantry increases the weight, volume and complexity of the CT system. Therefore, in accordance with an embodiment of the invention, FIG. 3 is a schematic diagram of a multichannel, contactless power transfer system 200. In lieu of a slip ring configuration, power from the stationary frame 13 is transferred to the rotating frame 12 by means of a multichannel, rotary transformer 202, which will be described in further detail hereinafter. Not only does the rotary transformer 202 transfer the primary x-ray generation power, but also the auxiliary power through one or more channels. In this manner, certain power conversion devices (such as inverters) can now be disposed on the stationary frame 13. For example, in addition to primary x-ray power inverter 108, system 200 further includes a separate auxiliary power inverter 204 mounted on the stationary frame 13.

Since the power produced by the x-ray power inverter 108 is of a pulsed nature, it is not suitable for supplying the various electronics present on the rotating frame 12 of the CT system 200. Thus, although the auxiliary power inverter 204 is similar to the x-ray power inverter, it has a reduced power capability with respect to the x-ray power inverter 108 (e.g., about 5 kW vs. about 150 kW). Another distinction between contactless system 200 and conventional system 100 is the use of equally split inductive and capacitive resonant elements in the two legs of the x-ray/auxiliary inverter outputs. Such a configuration helps to reduce common-mode voltage noise (generated by the IGBT switches) at the rotary transformer 202.

Instead of generating multiple, fixed voltage levels on the rotating frame, the rotary transformer 202 is configured to include an x-ray power primary winding 206 and secondary winding 208, as well as an auxiliary power primary winding 210 and one or more auxiliary power secondary windings 212, 214. It will be appreciated that multiple secondary windings may be integrated into the rotary transformer 202 to provide the various DC voltages desired (e.g., 600 VDC, 48 VDC, 24 VDC, etc.). In the particular embodiment depicted, voltages on each of the auxiliary power secondary windings 212, 214 are then rectified and filtered on the rotating frame 12 to create multiple DC voltages (i.e., a 600 volt, HV DC output for the rotor drive, and a 48 volt, low voltage DC output for various system electronics).

As further depicted in FIG. 3, the output voltages for the x-ray source, the high-voltage auxiliary source and the low-voltage auxiliary source may all be sensed, digitized and then transmitted from feedback collector/digitizer/transmitter 216 back to a stationary side power controller 218 through a capacitive or optical communication link, for example. One type of suitable contactless communications link is discussed in U.S. Pat. No. 6,301,324 to Pearson, Jr., et al., the contents of which are incorporated herein in their entirety. Such a feedback control loop allows the power controller 218 to control the IGBTs in the auxiliary power inverter 204 based upon the particular output voltage sensed on the rotating side that is experiencing the greatest percentage of voltage drop, thereby controlling multiple output voltages with one power inverter. Additional information in this regard may be found in U.S. Pat. No. 5,646,835 to Katcha, the contents of which are incorporated herein in their entirety.

Figure 4:
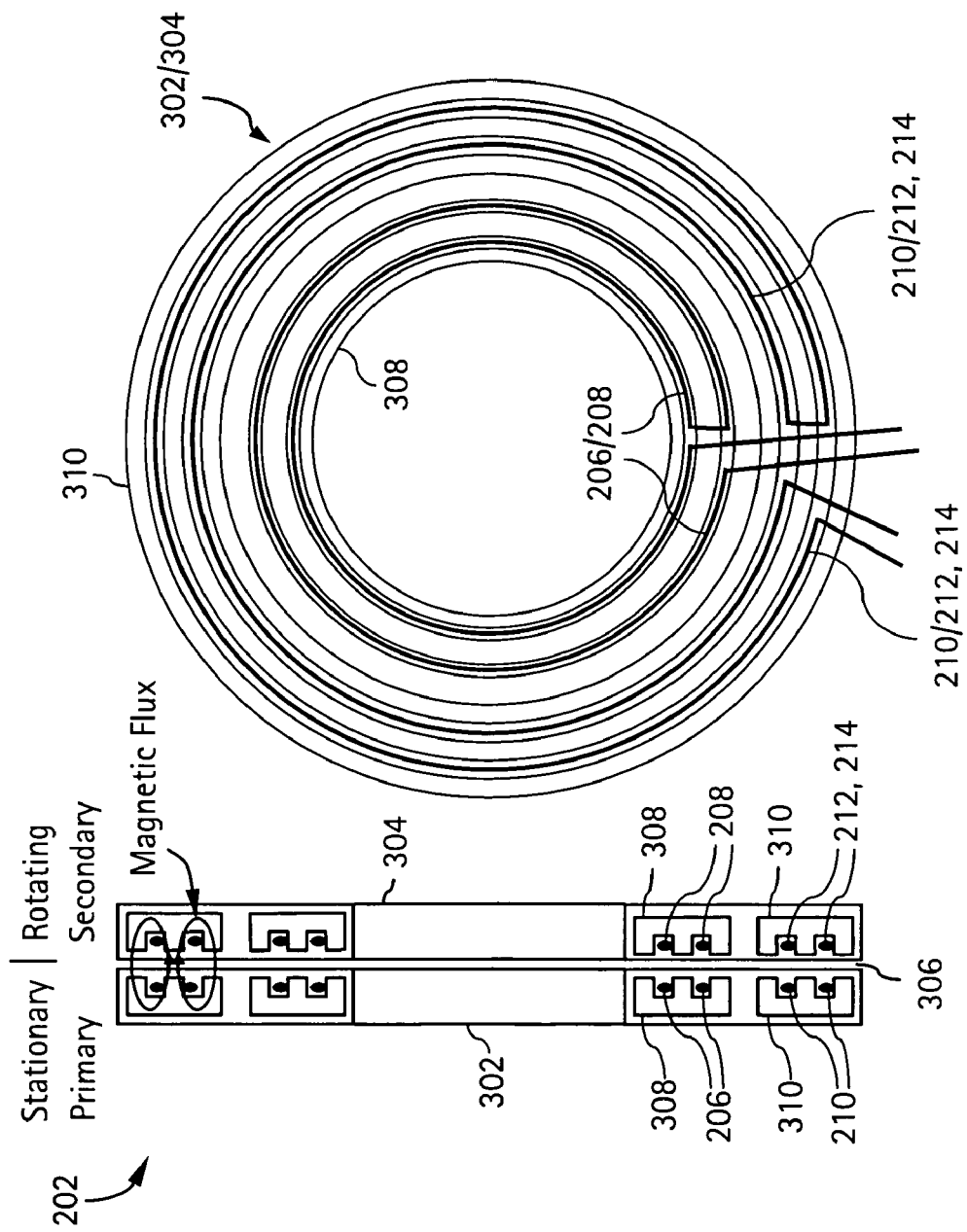
FIG. 4 is cross-sectional view of the multichannel, rotary transformer schematically depicted in FIG. 3.

Referring now to FIG. 4, there is shown a cross-sectional view of an embodiment of the rotary transformer 202 schematically depicted in FIG. 3. As is shown, the rotary transformer 202 features a pair of opposing platters, including a stationary (primary) platter 302 and a rotating (secondary) platter 304 having an air gap 306 therebetween. Each platter 302, 304 includes a pair of concentric cores (an inner core 308 for the primary/secondary x-ray power windings and an outer core 310 for the primary/secondary auxiliary power windings) made from a high magnetic permeability material (e.g., ferrite) that channels the magnetic flux from one platter to the other across the air gap 306. In the exemplary embodiment shown, the cores 308, 310 are "E-shaped" so as to better contain any stray magnetic fields in the vicinity of the cores.

As is further shown in FIG. 4, both the primary/secondary windings for the inner and outer E-shaped cores may be wound by beginning at one opening of the E-shaped core, winding around the platter in a first direction (e.g., clockwise) in one of the two channels of the E-shaped core to about the starling point, crossing over to another opening in the core, and winding back around the platter in the opposite direction (e.g., counterclockwise) in the other of the two channels back to the starting point, thereby completing one turn. It will be appreciated that multiple turns for both primary and secondary winnings (as well as multiple secondary windings) may be wound on the same E-shaped core, depending on the number of outputs and voltage levels desired.

Figure 5:
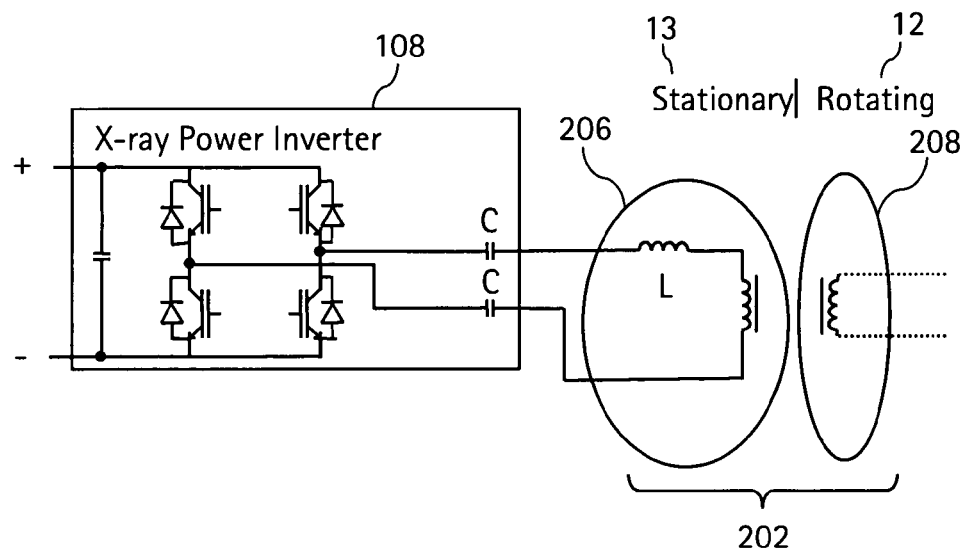
FIG. 5 is a schematic diagram of an alternative embodiment of the rotary transformer, in which a leakage inductance thereof serves as the resonant inductor of the power inverter.
Figure 6:
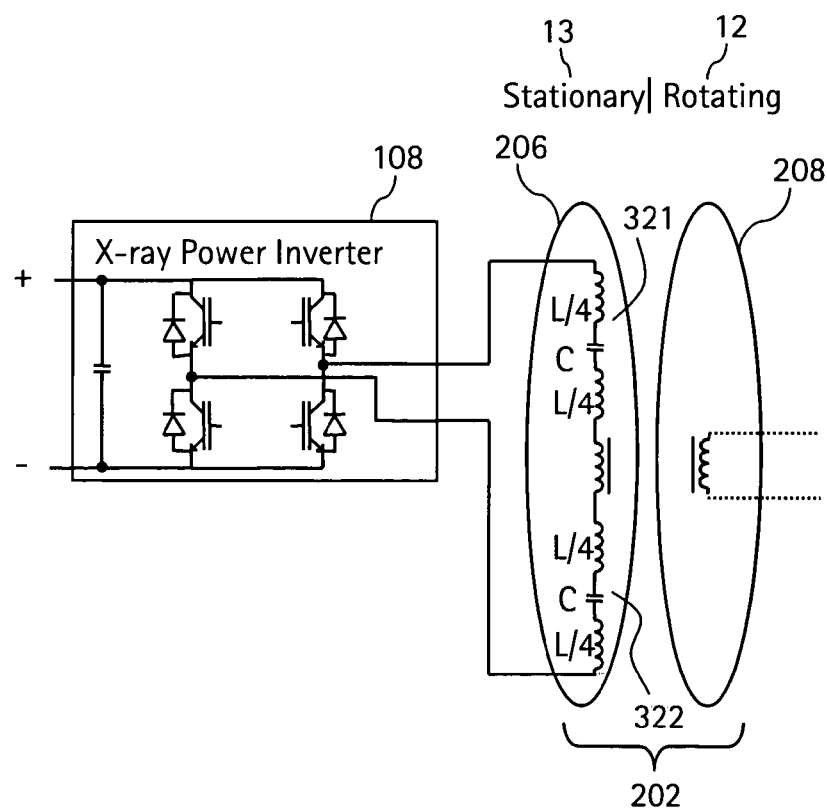
FIG. 6 is a schematic diagram of still another embodiment of the rotary transformer, in which resonant capacitors are also incorporated in the primary windings thereof.
Figure 7:
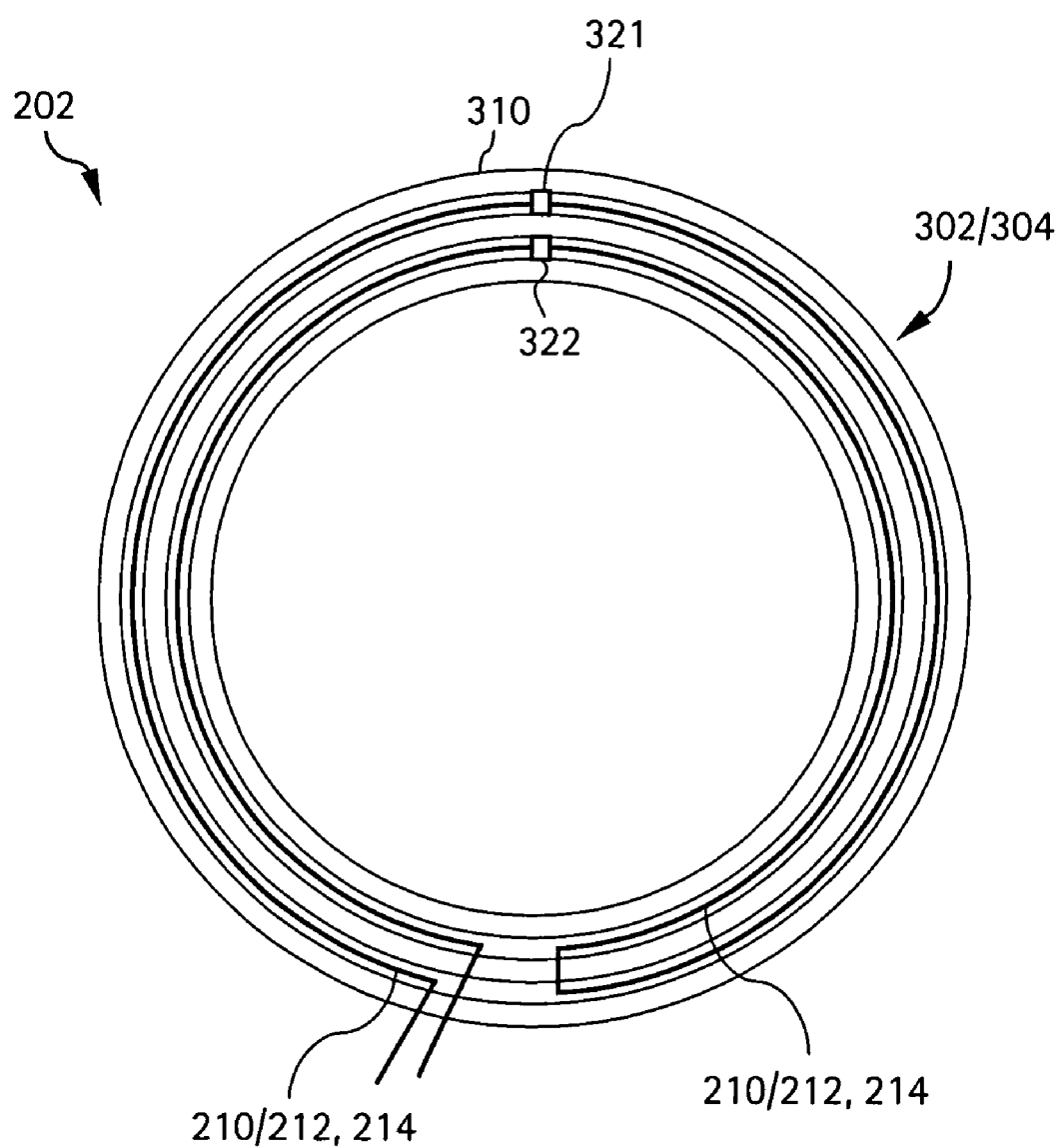
FIG. 7 is a cross-sectional view of the multichannel, rotary transformer schematically depicted in FIG. 6.

In an alternative embodiment shown in FIG. 5, the rotary transformer includes a leakage inductance, L, which serves as the resonant inductor of the power inverter 108, thereby eliminating a separate inductor component in the inverter housing. In still another alternative embodiment shown in FIG. 6, resonant capacitors 321, 322 are configured directly within the primary windings 206 of the rotary transformer 202, thus reducing the magnitude of the voltage experienced thereby. For example, for a one turn primary shown in FIG. 7, the capacitors 321, 322 may be placed at 180 degrees from the winding inputs, thereby minimizing the voltage experienced by the windings for the configuration of two resonant capacitors. This capacitor placement limits the resonant voltage developed by leakage inductance L. This configuration is exemplary only, and it should be appreciated by one skilled in the art that the particular configuration may be varied for different numbers of capacitors and primary turns for the purpose of reducing winding voltage.

Through the use of the above described multichannel, contactless power transfer system, the elimination of all contact slip ring brushes, associated dust, wear-out, and preventive maintenance needed results in advantageous cost savings. Furthermore, the removal of the x-ray power inverter assembly and bracket results in a direct reduction in the mass of from rotating frame of the system by about 40 kg. Correspondingly, there is also a counter-balance of equal weight that may also be removed from the rotating frame. With both the inverter and counter-balance removed, there is further room to eliminate cantilevered components so as to have a much more uniformly balanced gantry, thereby facilitating the achievement of a 0.2 sec/rev gantry speech. Still a further cost reduction stems from the placement of the inverter(s) and auxiliary DC-DC converters on the stationary side of the frame.

Moreover, by having multiple secondary windings on the rotary transformer results there is a further reduction in the complexity, number of parts, and volume of the system. In addition, the system provides reduced radiated electromagnetic emissions as a result of the split impedance in the inverter output legs and the configuration of the E-shaped rotary transformer core.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A multichannel, contactless power transfer system, comprising:
    a primary power inverter disposed on a stationary side of the system;
    an auxiliary power inverter disposed on said stationary side of the system;
    a rotary transformer having a primary side thereof disposed on said stationary side of the system and a secondary side disposed on a rotating side of the system; and
    said rotary transformer configured to couple primary power from an output of said primary power inverter to a primary power voltage output on said rotating side of the system, and said rotary transformer further configured to couple auxiliary power from an output of said auxiliary power inverter to at least one auxiliary voltage output on said rotating side of the system;
    a leakage inductance of said rotary transformer used as part of a resonant network for said primary power inverter; and a pair of resonant capacitors configured within said primary side of said rotary transformer, said resonant capacitors also comprising part of said resonant network for said primary power inverter.

2. The power transfer system of claim 1, wherein said primary and secondary sides of said rotary transformer further comprise concentric, E-shaped cores.

3. The power transfer system of claim 2, wherein:
a first of said concentric, E-shaped cores of said primary side of said rotary transformer is wound with a winding coupled to the output of said primary power inverter; and
a second of said concentric, E-shaped cores of said primary side of said rotary transformer is wound with a winding coupled to the output of said auxiliary power inverter.

4. The power transfer system of claim 3, wherein:
a first of said concentric, E-shaped cores of said secondary side of said rotary transformer is wound with a winding coupled to a tank circuit used to generate said primary power voltage output; and
a second of said concentric, E-shaped cores of said secondary side of said rotary transformer is wound with at least one winding used to generate said at least one auxiliary voltage output.

5. The power transfer system of claim 4, wherein each winding in said primary and said secondary sides of said rotary transformer is arranged by configuring a wire within first and second channels of a corresponding E-shaped core, beginning at a first opening in said corresponding E-shaped core, traversing circumferentially around said first channel, traversing a second opening in said corresponding E-shaped core, and traversing circumferentially around said second channel in the opposite direction to about said first opening.

6. The power transfer system of claim 1, wherein said primary power inverter further comprises a resonant network configured within a pair of output legs thereof.

7. The power transfer system of claim 6, wherein said auxiliary power inverter further comprises a resonant network configured within a pair of output legs thereof.

8. The power transfer system of claim 1, further comprising a power controller disposed on said stationary side, said power controller configured to receive digitized power output information from said primary power voltage output and said at least one auxiliary voltage output, transmitted through a contactless communications link, and wherein said power controller is further configured to maintain a desired voltage level for said primary power voltage output and said at least one auxiliary voltage output.

9. A multichannel, contactless power transfer system for a computed tomography (CT) system, comprising:
an x-ray power inverter disposed on a stationary side of the CT system;
an auxiliary power inverter disposed on said stationary side of the CT system;
a rotary transformer having a primary side thereof disposed on said stationary side of the CT system and a secondary side disposed on a rotating side of the CT system;
said rotary transformer configured to couple x-ray generation power from an output of said x-ray power inverter to a high-voltage tank circuit on said rotating side of the system, wherein said high-voltage tank circuit is further coupled to an x-ray generation tube; and
said rotary transformer further configured to couple auxiliary power from an output of said auxiliary power inverter to at least one auxiliary voltage output on said rotating side of the CT system;
a leakage inductance of said rotary transformer used as part of a resonant network for said primary power inverter; and
a pair of resonant capacitors configured within said primary side of said rotary transformer, said resonant capacitors also comprising part of said resonant network for said primary power inverter.

10. The power transfer system a claim 9, wherein said primary and secondary sides of said rotary transformer further comprise concentric, E-shaped cores.

11. The power transfer system of claim 10, wherein:
a first of said concentric, E-shaped cores of said primary side of said rotary transformer is wound with a winding coupled to the output of said x-ray power inverter; and
a second of said concentric, E-shaped cores of said primary side of said rotary transformer is wound with a winding coupled to the output of said auxiliary power inverter.

12. The power transfer system of claim 11, wherein:
a first of said concentric, E-shaped cores of said secondary side of said rotary transformer is wound with a winding coupled to said high-voltage tank circuit; and
a second of said concentric, E-shaped cores of said secondary side of said rotary transformer is wound with at least one winding used to generate said at least one auxiliary voltage output.

13. The power transfer system of claim 12, wherein each winding in said primary and said secondary sides of said rotary transformer is arranged by configuring a wire within first and second channels of a corresponding E-shaped core, beginning at a first opening in said corresponding E-shaped core, traversing circumferentially around said first channel, traversing a second opening in said corresponding E-shaped core, and traversing circumferentially around said second channel in the opposite direction to about said first opening.

14. The power transfer system of claim 9, further comprising a power controller disposed on said stationary side, said power controller configured to receive digitized power output information from said x-ray power voltage output and said at least one auxiliary voltage output, transmitted through a contactless communications link, and wherein said power controller is further configured to maintain a desired voltage level for said x-ray power voltage output and said at least one auxiliary voltage output.

15. A multichannel, contactless power transfer system for a computed tomography (CT) system, comprising:
an x-ray power inverter disposed on a stationary side of the CT system;
an auxiliary power inverter disposed on said stationary side of the CT system;
a rotary transformer having a primary side thereof disposed on said stationary side of the CT system and a secondary side disposed on a rotating side of the CT system;
said rotary transformer configured to couple x-ray generation power from an output of said x-ray power inverter to a high-voltage tank circuit on said rotation side of the system, wherein said high-voltage tank circuit is further coupled to an x-ray generation tube, said rotary transformer further configured to couple auxiliary power from an output of said auxiliary power inverter to at least one auxiliary voltage output on said rotating side of the CT system;
said x-ray power inverter further comprising a resonant network configured within a pair output legs thereof;

said auxiliary power inverter further comprises a resonant network configured within a pair of output legs thereof; and wherein said resonant network in said x-ray power inverter and said auxiliary power inverter further comprises a plurality of inductive and capacitive elements equally divided between said pair of output legs.

16. A contactless power transfer system, comprising:

a primary power inverter disposed on a stationary side of the system;

a rotary transformer having a primary side thereof disposed on said stationary side of the system and a secondary side disposed on a rotating side of the system;

said rotary transformer configured to couple primary power from an output of said primary power inverter to a primary power voltage output on said rotating side of the system;

a leakage inductance of said rotary transformer used as part of a resonant network for said primary power inverter; and a pair of resonant capacitors configured within said primary side of said rotary transformer, said resonant capacitors also comprising part of said resonant network for said primary power inverter.

* * * * *

UNITED STATES PATENT AND TRADEMARK OFFICE
CERTIFICATE OF CORRECTION

PATENT NO. : 7,054,411 B2  Page 1 of 1
APPLICATION NO. : 10/708934
DATED : May 30, 2006
INVENTOR(S) : Jason Stuart Katcha et al.

It is certified that error appears in the above-identified patent and that said Letters Patent is hereby corrected as shown below:

Column 6,
Line 23, after "gantry", delete "speech" and insert therefor --speed--.

Column 7,
Lines 64-65, after "tube;", delete "and".

Column 8,
Line 59, after "said", delete "rotation" and insert therefor --rotating--.
Line 67, after "pair", insert --of--.

Signed and Sealed this

Twelfth Day of December, 2006

JON W. DUDAS
*Director of the United States Patent and Trademark Office*